United States Patent [19]
Griebel

[11] Patent Number: 4,982,738
[45] Date of Patent: Jan. 8, 1991

[54] DIAGNOSTIC APNEA MONITOR SYSTEM

[75] Inventor: Peter Griebel, Freiburg, Fed. Rep. of Germany

[73] Assignee: Dr. Madaus GmbH, Cologne, Fed. Rep. of Germany

[21] Appl. No.: 278,139

[22] Filed: Nov. 30, 1988

[51] Int. Cl.⁵ .............................................. A61B 5/02
[52] U.S. Cl. .................................... 128/670; 128/671; 128/766; 128/716
[58] Field of Search ............... 128/630, 668, 670, 671, 128/706, 709, 710, 711, 716, 739, 773

[56] References Cited

U.S. PATENT DOCUMENTS

| | | | |
|---|---|---|---|
| 3,572,317 | 3/1971 | Wade | 128/723 |
| 4,053,951 | 10/1977 | Hudspeth et al. | 128/670 |
| 4,305,400 | 12/1981 | Logan | 128/670 |
| 4,333,475 | 6/1982 | Moreno et al. | 128/711 |
| 4,452,252 | 6/1984 | Sackner | 128/671 |
| 4,580,575 | 4/1986 | Birnbaum et al. | 128/723 |
| 4,686,999 | 8/1987 | Snyder et al. | 128/671 |
| 4,777,962 | 10/1988 | Watson et al. | 128/716 |
| 4,827,943 | 5/1989 | Bornnet et al. | 128/668 |

Primary Examiner—Randall L. Green
Assistant Examiner—K. Reichle
Attorney, Agent, or Firm—Felfe & Lynch

[57] ABSTRACT

In a method of diagnosing obstructive sleep apnea, snoring and respiration sounds made by a patient, as well as the patient's heart rate, are recorded while the patient is sleeping. Signals indicative of snoring sounds and the time intervals therebetween are produced from the respiration sounds and recorded, and a first respiration disturbance index representing the number of intervals per hour between episodes of snoring is calculated. Signals indicative of the patient's heart rate are likewise produced and recorded, and the average heart rate is calculated. A second respiration disturbance index representing the number of episodes per hour in which the patient's heart rate remained at 90 to 109% of its average rate is calculated. A physician can then evaluate the first and second disturbance indices to determine whether obstructive apnea is indicated.

Apparatus for practicing the method is also disclosed.

4 Claims, 6 Drawing Sheets

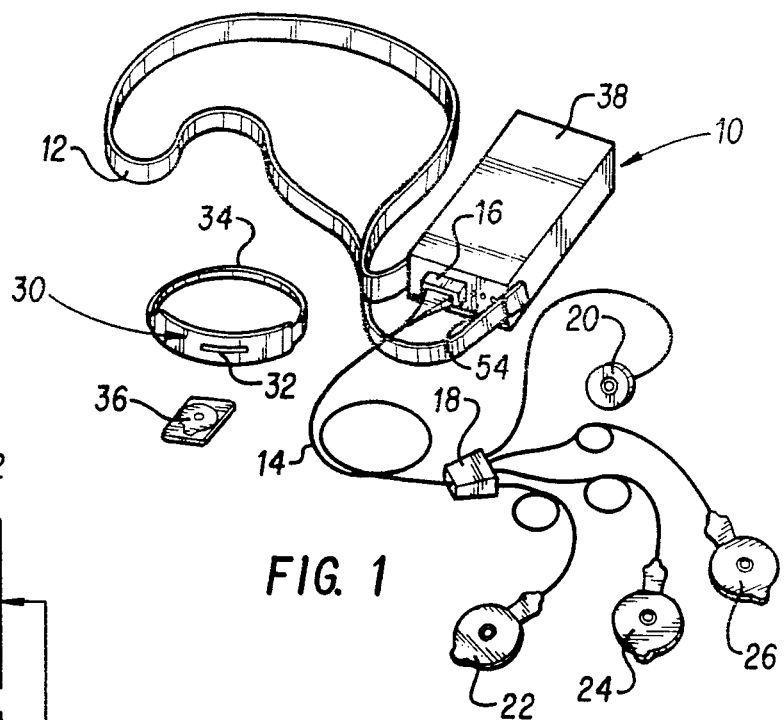
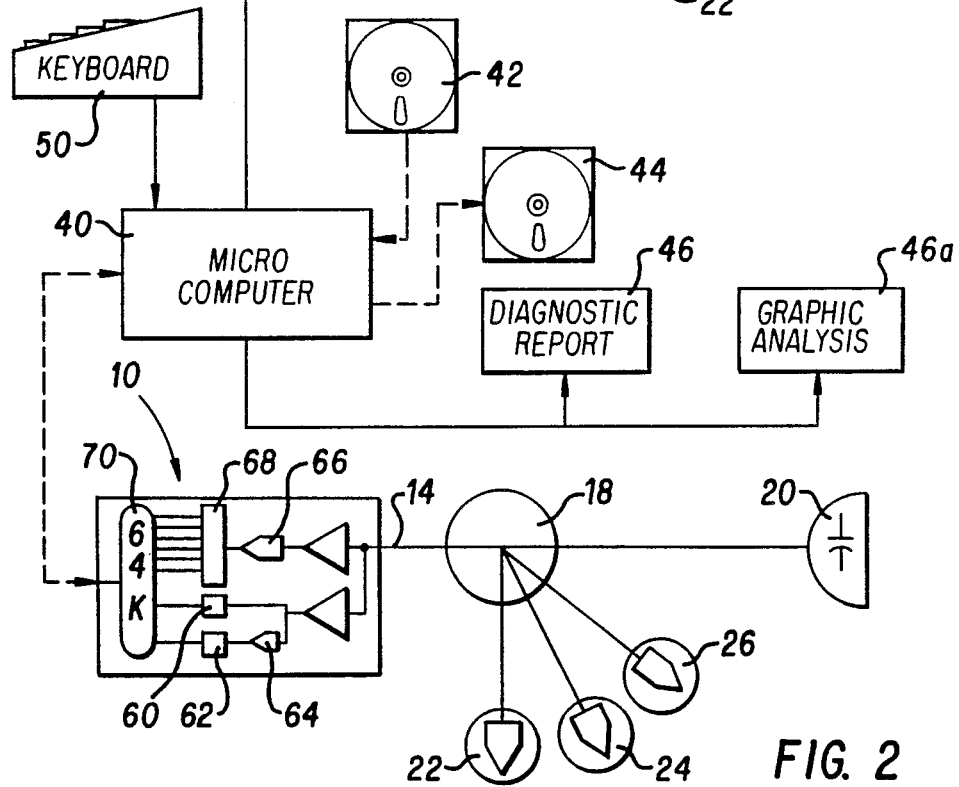
FIG. 1
FIG. 2

```
                      DIAGNOSTIC REPORT

Family name:  Doe                    PID - Nr.     : 666-66-6666
First name :  John                   Sex           : M
D. of birth:  17.9.51                Height        : 182 cm
Address    :  66 Seminole Drive      Weight        : 70  kg
           :  Philadelphia PA 19000  Broca         : 85 %
Telephone  :  666-6666               diast. value: 95  mmHg
Doctor     :

Results of the symptom evaluation:

An evaluation is not possible

Results of the long term recording : No. 3 from 3.8.1988

The evaluated time was              : from 00:00:00 to 04:00:00
The average heart rate was          : 48 bpm  Evaluation 100%
With a standard deviation of        : 6
RDI from the constant heart rate    : 59   phases/hr
RDI from the snore interval time    : 18   phases/hr Results:

Date                Signature
```

FIG. 3

| TIME | AVERAGE HEART RATE | STANDARD DEVIATION | HISTOGRAM |
|---|---|---|---|
| 00:00 | 51 | 8 | |
| 00:10 | 54 | 9 | |
| 00:20 | 49 | 7 | |
| 00:30 | 46 | 3 | |
| 00:40 | 46 | 3 | |
| 00:50 | 45 | 2 | |
| 01:00 | 45 | 2 | |
| 01:10 | 51 | 9 | |
| 01:20 | 49 | 7 | |
| 01:30 | 47 | 5 | |
| 01:40 | 48 | 3 | |
| 01:50 | 52 | 2 | |
| CON. | 48 | 6 | 31-     161- |

DIAGNOSTIC APNEA MONITOR SYSTEM

BACKGROUND OF THE INVENTION

1. Field of the Invention

The invention is related to methods and apparatus for diagnosing sleep disorders. More particularly, the present invention is directed to ambulatory diagnostic apparatus and methods for use in treating sleep apnea.

2. Discussion of Related Art

A coincidence of a reduction in active changes of electrical heart and respiration potentials for a substantial length of time, followed by an increase in heart rate, is known to be an indication of sleep apnea. However, this type of record is subject to electrical potential artifacts that compromise the usefulness of these signals, as noted in U.S. Pat. Nos. 4,422,458 and 4,580,575. Also, snoring itself may be a risk factor when obstructive sleep apnea is suspected, depending on its pattern, and such devices cannot evaluate this condition. Also different types of sleep apnea, such as obstructive apnea and centrally caused apnea, are amenable to different therapeutic measures. These devices cannot provide the differential diagnosis needed for treatment of an apnea patient's problem.

The use of acoustic screening of respiration by a behavior modification device that detects loud snoring, or an alarm device that wakes the patient when a period of silence occurs that indicates a dangerously long acute sleep apnea episode, is disclosed in U.S. Pat. No. 4,715,367. Other acoustic alarm devices are disclosed in U.S. Pat. Nos. 4,306,567 and 4,129,125.

Snoring is generally known to be an indicator of obstructive apnea, as distinct from neurological, centrally-caused apnea. However, the occurrence of snoring and silence, either in combination or separately, does not provide sufficient information to provide a diagnosis that is adequate for the treatment of sleep apnea. For example, some brief, non-acute sleep apnea episodes disturb sleep, and can produce symptoms such as fatigue and irritability that are cumulative and can become clinically significant. However, similar silences may be detected that are not indicative of sleep apnea—because of the acoustic difference between thoracic and abdominal breathing.

Prompt, accurate diagnosis of sleep apnea is also important because sleep apnea is a condition that can be treated, and even corrected, if it is detected and the nature of the problem causing it is identified early enough. Also, sleep apnea episodes that are not themselves life threatening are, nonetheless, a serious risk factor for the survival of cardiac patients. Early, accurate diagnosis and prompt treatment of sleep apnea is particularly important for these high-risk apnea patients.

Thus, when sleep apnea is suspected, the patient is commonly referred to a hospital "sleep center," which can provide a complete diagnosis of the patient's condition during sleep, based on a detailed, polysomnographic record. However, polysomnographic evaluation—which monitors thoracic air pressure, partial (P) and saturated (Sa) blood oxygen pressure, abdominal and thoracic respiration potentials, breath sounds, heart rate, and possibly other indicators as well—must be done on an in-patient basis.

Of course, such a hospital stay is expensive. It is also disruptive of the patient's daily routine in a way that may, in itself, produce sleep disturbances. Such additional disturbances may generate misleading results, and could possibly interfere with diagnosis of the underlying cause of a patient's clinical symptoms. Furthermore, the manual review process required to evaluate the voluminous, detailed record thus produced is both highly technical and very time-consuming.

It has been surprisingly found that the automated report provided in accordance with the present invention has produced no false negative indications despite its much greater simplicity and compactness, when that report is evaluated by skilled medical personnel. The invention also, surprisingly, has provided a complete diagnosis for 54% of the patients tested. For the remainder, the invention permits medical personnel to limit the number of patients referred for full polysomnographic evaluation to cases where centrally-caused apnea is indicated.

SUMMARY OF THE INVENTION

Ambulatory diagnostic recording apparatus includes means for sensing cardiac potentials, means for detecting heart rate from said cardiac potentials, means for detecting respiration and snoring sounds and means for recording encoded signals representing the heart rate and the detected sounds.

A diagnostic system for diagnosing obstructive sleep apnea in accordance with the present invention includes this ambulatory diagnostic recording apparatus, means for computing first and second respiration disturbance indexes from said encoded signals, and means for formatting reports including a chart of the frequency distribution of periods of silence and periods of stable heart rate and a chart of the temporal relationship between the recorded heart rate and the occurrence of the respective detected sounds.

The method of diagnosing obstructive sleep apnea in accordance with the present invention computes two respiration distress indexes, derived from encoded signals representing the patient's heart rate and the occurrence of respiration sounds made by the patient, as well as formatting charts of the frequency distribution and temporal coincidence of changes in the recorded signals.

The apparatus and method provides an inexpensive, highly-automated, ambulatory diagnostic evaluation that has proven to be effective in identifying high-risk patients.

The present invention also very accurately distinguishes those patients having symptoms that appear to be similar to the symptoms of apnea, but which have a different etiology from apnea patients. Thus, the therapy that is appropriate for these apnea patients can be more readily identified. Moreover, because the invention provides a highly reliable positive diagnosis of obstructive sleep apnea, expensive polysomnographic evaluation limited to apnea patients having centrally-caused apnea that requires further testing for determining the appropriate therapy.

For many apnea patients the present invention also permits sleep apnea to be treated earlier, when apnea treatment is more likely to be effective, since their diagnosis can be established with level of confidence through this out-patient procedure, making the cost and inconvenience of an in-patient polysomnographic evaluation unnecessary. Also, for many patients, the present invention reduces the risk of complications arising because its low-cost and diagnostic effectiveness permits treatment of the problem before a patient's clinical symptoms become severe enough to justify referring the patient to a sleep center.

Another advantage of the present invention is the simplicity of the ambulatory apparatus required for this highly-effective, automated diagnostic evaluation. The recording unit is physically not unlike familiar audio devices, and its operation requires no intervention by the patient. The timing control for the recording session is preset by medical personnel.

Another advantage of the present invention is that all data transfer and data evaluation, charting and reporting procedures are all automated. All actions required occur in response to prompts displayed on the screen of a standard personal computer. Furthermore only very select, specific information is recorded and reported, unlike the diagnostic methods now in use.

Another advantage of the invention is the familiar, non-invasive character of the sensors that are used for this screening. These sensors can be successfully applied and worn by adult patients without assistance. The sensors and the recording units can also be worn by the patient under street clothes, if necessary.

BRIEF DESCRIPTION OF THE DRAWINGS

FIG. 1 is a perspective view of the patient screening apparatus;

FIG. 2 is a schematic diagram of the diagnostic system;

FIG. 3 is an example of a diagnostic report for a first patient;

DESCRIPTION OF A PREFERRED EMBODIMENT

Figure 4:
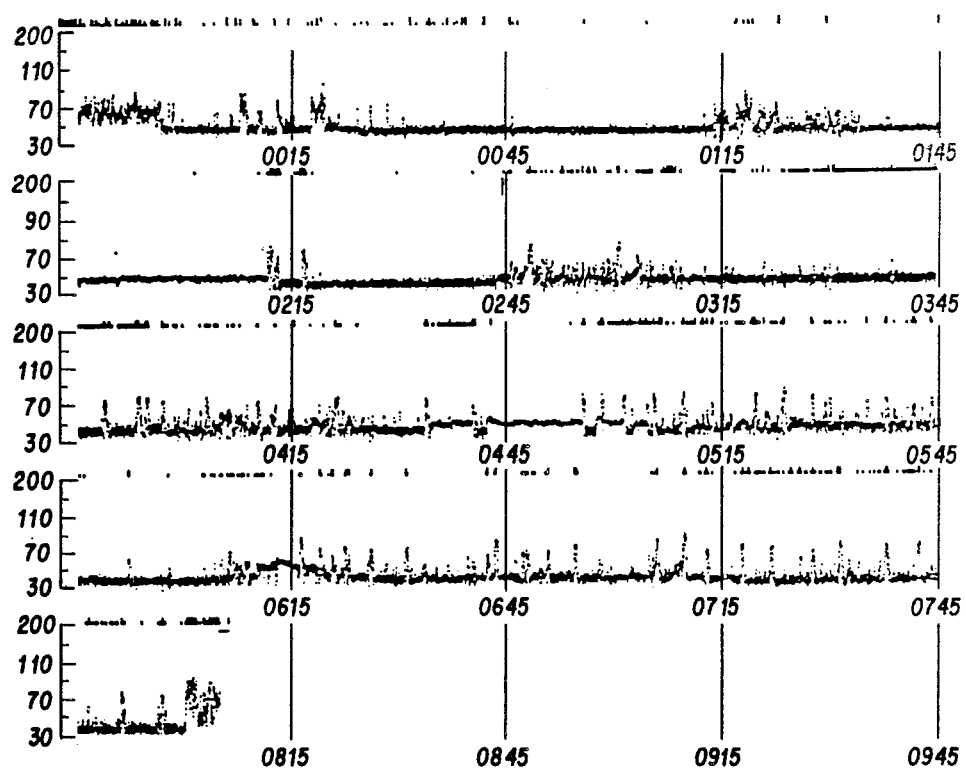
FIG. 4 is a plot of heart rate, breath sounds, and snoring over an 8 hr. 21 mins. and 26 secs. period from 11:45 p.m. to 8:06:26 a.m.

The patient monitor, shown in FIG. 1, comprises a light-weight, battery-powered data recording unit 10 that contains 64 K of random access memory. The recording unit 10 has a lanyard 12 which permits the data storage unit 10 to be suspended from the patient's shoulder. The recording unit 10 is small in size as well as light in weight—30 mm thick, 160×90 mm on its face, and weighing approximately 300 grams without batteries.

A patient data cable 14 is provided, having a multi-pin connector 16 which is affixed to the recording unit 10 by two screws. The data cable 14 ends in a cable junction 18. A small, disc-shaped electret microphone 20 and three EKG electrodes 22, 24, 26 are attached to the cable junction 18.

The patient monitor also includes a polypropylene band 30 having a slit 32 through which the electret microphone 20 is inserted after the band 30 is fastened around the patient's neck using a hook and loop "VEL-CRO" fastener 34. The band is then adjusted so that the microphone 20 rests against the patient's larynx. The face of the microphone 20 that rests against the patient's larynx has an annular, insulative cushioning layer thereon that is covered by a disposable, annular self-adhesive cover 36. The lanyard 12 of the data recording unit 10 is attached to a shoulder holster 38 which is also insulated and cushioned to minimize patient discomfort.

Referring to FIG. 2, the breath sound signal from the electret microphone is provided to two threshold detectors 60, 62. The first detector 60 determines whether the acoustic signal from the electret microphone 20 reaches a level that corresponds to the patient's normal breathing sound. The signal from the electret microphone is also supplied to a second threshold detector 62 through a filter 64 that provides 12 dB per octave signal attenuation above 800 Hz. The second threshold detector determines when this filtered signal reaches a level that corresponds to the patient's snoring sounds.

The EKG potential signal is detected differentially by two active electrodes 22 and 24, relative to the potential of a reference electrode 26, in accordance with standard clinical practice. The EKG signal is then supplied to a peak-detector circuit 66 that measures the peak-to-peak interval between R-wave potentials in the EKG signal. The value of the most recent interval is determined each second and encoded by a sample-and-hold circuit 68.

These samples are then recorded by the random access memory 70 as an eight-bit word for each sample. Two bits indicate the occurrence within a sample period of breath sounds and snoring, respectively, and six bits represent the value of the peak-to-peak interval in that sample period. The accuracy of the heart rate value thus encoded in a preferred embodiment of the present invention is specified as shown in Table 1.

TABLE 1

| Heart rate | Resolution |
|---|---|
| 0-20 bpm | 20 bpm |
| 21-30 bpm | 5 bpm |
| 31-130 bpm | 2 bpm |
| 131-160 bpm | 5 bpm |
| 161-200 bpm | 10 bpm |

The recording unit 10 continuously stores these samples over an 18 hour period. The recording sessions are usually set to begin between 6 P.M. and midnight on the day when the preprogramming is done, depending on the patient's individual, customary sleep schedule.

The multi-pin connector 16 on the recording unit 10 described above is compatible with an RS232 standard, 9600 baud, computer interface and interface cable (not shown). During the follow-up session, after the recording is complete, the recording unit 10 is connected through this connector 16 to a personal computer 40—preferably a standard, IBM-XT or AT compatible computer—as shown in FIG. 2. Because, as a safety measure, the same connector 16 on the recording unit 10 is used for both cables, the patient cannot be accidently connected through the recording unit 10 to the computer 40 that could transmit a dangerous electric shock to the patient.

A menu-driven data analysis and report formatting computer program is provided on a software diskette 42 which can be loaded into the microcomputer 40. The program automatically controls the administrative procedures required to obtain a preliminary screening determination, analyzes the data provided by the recording unit 10, calculates diagnostic indexes and statistical data for the diagnostic report 46 (FIG. 3) and charts 46a (FIGS. 4-7) and then prints them on command.

A patient who may have apnea is first put through a pre-screening procedure. The patient is weighed, measured and checked for hypertension. Patient identification data is then entered at the computer keyboard 50 by medical personnel along with the patient's current height, weight and diastolic blood pressure, in response to prompts on the computer screen 52.

The computer program then performs a step-by-step interview routine, using either the standard apnea pre-screening questionaire formulated by the West German Society of Pneumology or an equivalent anamnesis questionaire. The patient responds either YES or NO to questions as they appear on the computer screen 52 by pressing #1 or #2 on the keyboard 50, respectively. For example:

| | | |
|---|---|---|
| 1. | Has your partner noticed that your breathing stops during sleeping? | |
| ( ) | 1 - YES | (positive indication) |
| ( ) | 2 - NO | (continue questionnaire) |
| 2. | Do you find it difficult to go to sleep? | |
| ( ) | 1 - YES | (−1 point) |
| ( ) | 2 - NO | (0 points) |
| 3. | Do you take sleep medicines? | |
| ( ) | 1 - YES | (−1 point) |
| | 2 - NO | (0 points) |
| 4. | Both YES/one YES | (+1 point) |
| | Both NO | (0 points) |
| a. | Do you often snore | |
| ( ) | 1 - YES | |
| ( ) | 2 - NO | |
| b. | When you snore, do you snore loudly and irregularly? | |
| ( ) | 1 - YES | |
| ( ) | 2 - NO | |
| 5. | One to three times YES | (+1 point) |
| | Three times NO | (0 points) |
| a. | Are you liable to fall asleep during the day? | |
| ( ) | 1 - YES | |
| ( ) | 2 - NO | |
| b. | Do you have difficulty staying awake, even when you do not want to completely relax, e.g., when reading or watching television? | |
| ( ) | 1 - YES | |
| ( ) | 2 - NO | |
| c. | Do you often feel tired and exhausted? | |
| ( ) | 1 - YES | |
| ( ) | 2 - NO | |

The patient's answers and physical condition are then scored automatically by the computer, as indicated in Table 2.

TABLE 2

| Points scored | Statement |
|---|---|
| −3, −2 or −1 | Indication negative, findings unlikely. |
| 0 or +1 | Indication positive, findings questionable. |
| +2 or +3 | Indication positive, findings likely. |

The computer displays the statement that apnea findings are "likely" or "questionable" or "unlikely", that is automatically associated with the patient's numerical score through a lookup table in the computer program.

Recording units are only provided when the computer indicates that apnea is "likely" or "questionable," to avoid delaying other, further tests when apnea is unlikely. The recording unit is then pre-programmed before the recording session, the patient is instructed in the use of the sensor devices, and a follow-up session is scheduled for data retrieval and analysis.

The recording unit is automatically pre-programmed by attaching it to the computer 40 through an interface cable (not shown). Medical personnel select the time at which recording will begin and indicate the date and identifying number of the recording session through the keyboard 50 in response to prompts displayed on the screen 52. The computer then erases any previous data remaining in the recording unit 10 and enters a 256-character label into the memory of the recording unit 10. The label is automatically derived by the computer program from the preliminary screening data previously entered, and positively identifies both the recording session and the patient.

The patient is then instructed how to apply the microphone and EKG electrodes during this pre-programming procedure and, when the microphone and electrodes are in place, the unit's operability is tested using three LED indicator lights 54 located on the recording unit 10. One of these lights responds when the patient simulates episodes of snoring, and another responds to normal breathing sounds but stays dark when the patient stops breathing momentarily. This tests the microphone and the street amplifier, filtering and detector circuits respectively. The third responds in cadence with the patient heart beat, as reflected by the peaks of the signal provided by the EKG electrodes. Checking the rhythm of this light's response tests the sensor electrodes and the EKG amplifier peak-detector circuits.

These three lights 54 are active for 5 minutes each time the patient data cable 14 is attached to the recording unit 10. After 5 minutes the lights are automatically switched off to conserve battery power.

In the follow-up session, medical personnel retrieve the patient's preliminary screening data from the computer's memory, and format a new patient diskette 44 according to prompts supplied by the programs on the computer screen. The program automatically records a 256-character label on the diskette. This label is also derived from the patient's pre-screening data in the same way as the label supplied to the memory 70 of the recording unit 10 before the recording session was recorded by the computer in the recording unit during pre-programming.

When the recording unit 10 is connected to the computer 40 the analysis program on the software diskette 42 first checks whether the label just recorded on the new patient diskette 44 matches the old label found in the memory of the recording unit 10. If the labels match, the program then copies the raw data provided by the recording unit 10 through the interface cable (not shown) onto the pre-formatted 360 kB patient diskette 44. This procedure lasts about 90 seconds.

After the recorded signals have been copied, the programs then automatically calculate two respiration disturbance indexes (RDI) from the recorded data for printing as a diagnostic report, such as the sample report shown in FIG. 3, as well as formatting charts of the raw data and statistical analysis of that data, such as those shown in FIGS. 4 through 7.

The first RDI value is the number of time intervals per hour between episodes of snoring. The second RDI value is the number of time intervals per hour in which the patient's pulse rate remained at 90% to 109% of its average rate. That average rate is computed for each recording session. The time criterion for both RDI values limit these indexed to time intervals lasting from 11 to 60 seconds. Intervals that are shorter or longer are not counted. These values are reported in the section headed "Results of the long-term recording" in FIG. 3.

The computer program also reports the result of the questionaire in the section headed "Results of the symptom evaluation" listing scores of "0" or "±1" in the categories listed in Table 3.

TABLE 3

(1) Difficulty in Falling Asleep
(2) Sleep Medication
(3) Snoring
(4) Wakefulness
(5) Fitness factors One of the fitness factors is the "Broca index" is an obesity index, which derived from the relationship between the patient's weight and height. The other fitness factor is the diastolic blood pressure. When the screening questionaire is omitted, the computer prints out "An evaluation is not possible" in place of this symptom evaluation. This is the case in FIG. 3, however, the testing procedure was undertaken anyhow.

The charts shown in FIGS. 4 through 7 are examples of charts that can be selected by the patient's physician for use in generating the diagnostic report shown in FIG. 3. All of these charts represent data monitored for a single patient during a given eight hour twenty-one minute and twenty-six second period. The signal tracings in FIG. 4 show the recorded data for the entire session from 11:45 p.m. to 8:06:26 a.m. Periods having unusual signal patterns are clearly shown on this compressed chart. The broken line above the "200" in each pair of traces shows two sound detection bits. The lower bit appears when breath sounds are detected. The upper bit appears when snoring is detected.

Figure 5:
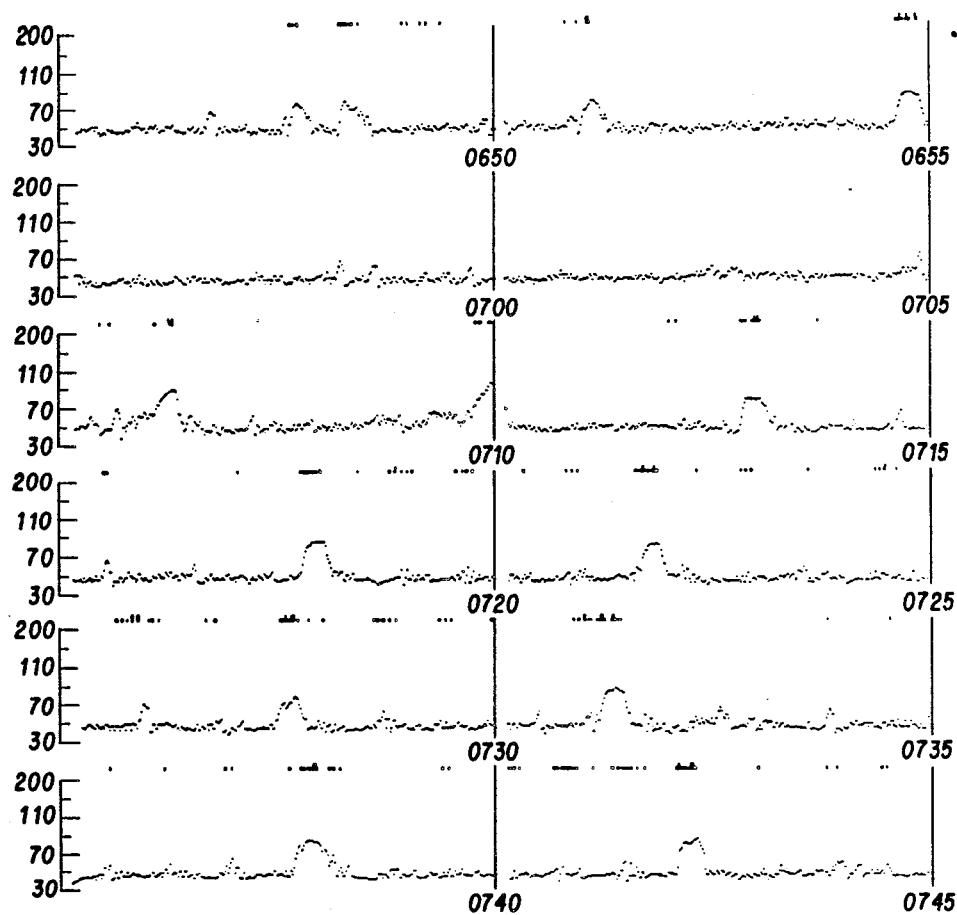
FIG. 5 is a detailed plot of heart rate, breath sounds, and snoring from 6:45 to 7:45 a.m.
Figures 6A, 6B:
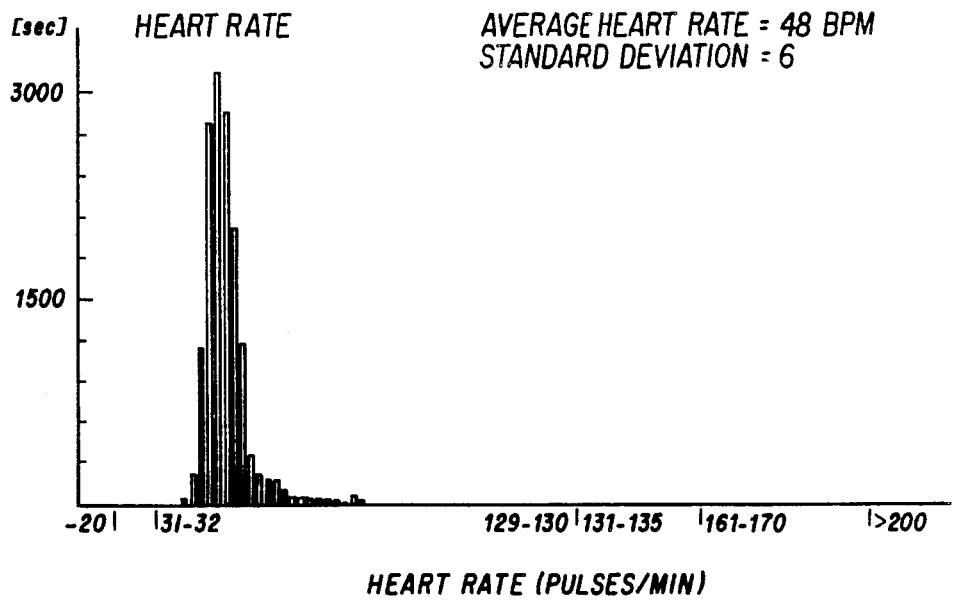
FIG. 6A shows the average heart rate and histogram during ten minute intervals over the two hour period 12 to 2 a.m.
FIG. 6B shows the heart rate distribution (time at each rate) during the two hour period.
Figure 7A:
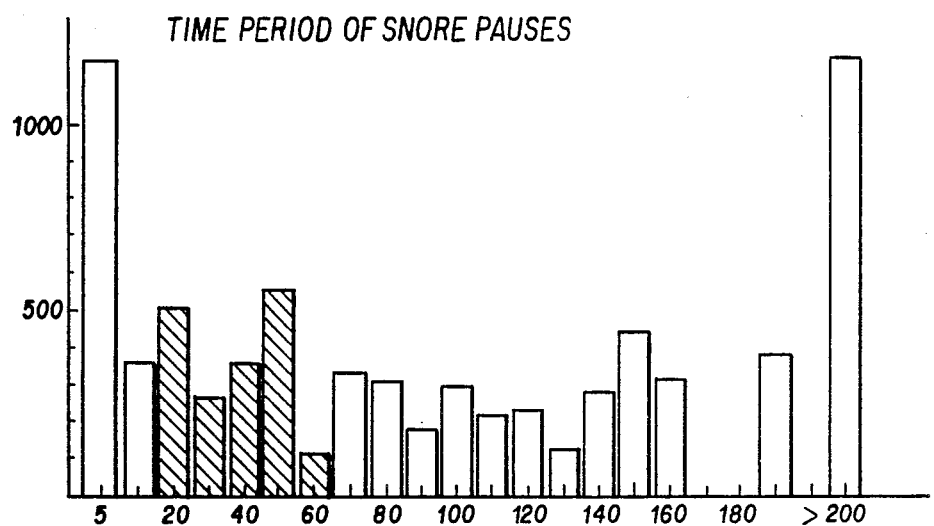
FIG. 7A shows the snore pause distribution (time at each length of snore pause) over four hours from 12 to 4 a.m.
Figure 7B:
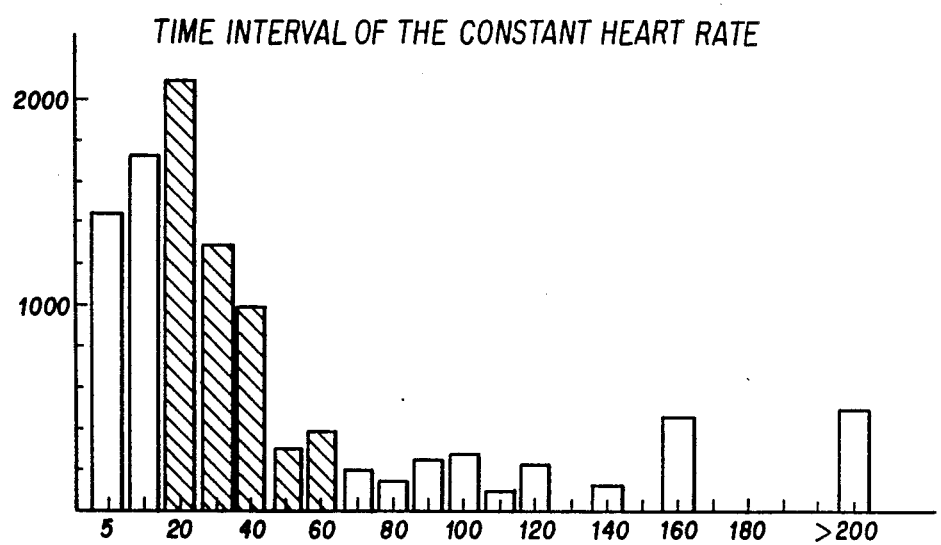
FIG. 7B shows heart rate distribution (time at each interval of constant heart rate) over the four hours.

In FIG. 5, the period between 6:45 a.m. and 7:45 a.m. has been selected from the recording session shown in FIG. 4, for detailed study of an erratic pattern. The histograms of FIG. 6A and the heart rate distribution of FIG. 6B represent the period from midnight to 2 a.m. FIG. 7A shows the snore pause distribution and FIG. B shows the heart distribution; after between midnight and 4:00 a.m. This time period will be automatically selected for charting by the analysis program, since it is usually a period of deep sleep for patients. Heart rate and breathing patterns during REM sleep occurring after 4 a.m., on the other hand are likely to be highly variable, due to dream activity. In deep sleep these patterns become very smooth and regular, which makes disruptions caused by apnea highly visible.

The invention has been disclosed above with particular reference to a presently preferred embodiment of the invention. However, the method and apparatus in accordance with the present invention are defined by the appended claims. Those skilled in the art will recognize that modifications and variations of the disclosed embodiment can be made within the spirit and scope of the invention recited in the claims. For example, an additional parameter might be sampled and recorded to assist in achieving an adequate diagnosis of centrally-caused apnea without resorting to polysomnography.

I claim:

1. Method of diagnosing obstructive sleep apnea in a patient, comprising the steps of:
   detecting breathing sounds made by the patient, and the patient's heart rate, while the patient is sleeping;
   producing from said breathing sounds, signals indicative of snoring sounds and the time intervals therebetween;
   recording said snoring sounds and the time intervals therebetween;
   calculating a first respiration disturbance index representing the number of time intervals per hour between episodes of snoring;
   producing signals indicative of the patient's heart rate;
   recording said heart rate,
   calculating the average heart rate and a second respiration disturbance index representing the number of time intervals per hour in which the patient's heart rate remained within a given deviation from its average rate,
   evaluating said first and second respiration disturbance indices to determine whether obstructive apnea is indicated.

2. Method as in claim 1 wherein the second respiration disturbance index represents the number of time intervals per hour in which the patient's heart rate remained at 90% to 109% of its average rate.

3. Method as in claim 1 wherein time intervals shorter than 11 seconds or longer than 60 seconds between episodes of snoring are not counted in calculating the first respiration disturbance index.

4. Method as in claim 1 wherein time intervals shorter than 11 seconds or longer than 60 seconds of constant heart rate are not counted in calculating the first respiration disturbance index.

* * * * *

UNITED STATES PATENT AND TRADEMARK OFFICE
CERTIFICATE OF CORRECTION

PATENT NO. : 4,982,738
DATED : January 8, 1991
INVENTOR(S) : Peter Griebel It is certified that error appears in the above-identified patent and that said Letters Patent is hereby corrected as shown below:

Column 2, line 57, insert --can be-- before "limited".

Signed and Sealed this

Thirteenth Day of July, 1993

*Attest:*

MICHAEL K. KIRK

*Attesting Officer*   *Acting Commissioner of Patents and Trademarks*